(12) United States Patent
Thyng

(10) Patent No.: US 10,288,534 B1
(45) Date of Patent: May 14, 2019

(54) METHOD OF FLUID SAMPLING AND DEVICE THEREOF

(71) Applicant: Frederick Matthew Thyng, Kittery Point, ME (US)

(72) Inventor: Frederick Matthew Thyng, Kittery Point, ME (US)

( * ) Notice: Subject to any disclaimer, the term of this patent is extended or adjusted under 35 U.S.C. 154(b) by 3 days.

(21) Appl. No.: 16/059,089

(22) Filed: Aug. 9, 2018

Related U.S. Application Data

(60) Provisional application No. 62/664,962, filed on May 1, 2018.

(51) Int. Cl.
| | | |
|---|---|---|
| *G01N 1/14* | (2006.01) | |
| *G01N 1/18* | (2006.01) | |
| *G01N 35/10* | (2006.01) | |
| G01N 35/00 | (2006.01) | |
| G01N 1/00 | (2006.01) | |

(52) U.S. Cl.
CPC ............. *G01N 1/14* (2013.01); *G01N 1/18* (2013.01); *G01N 35/1009* (2013.01); *G01N 35/1097* (2013.01); G01N 2001/002 (2013.01); G01N 2001/1427 (2013.01); G01N 2035/00277 (2013.01); G01N 2035/00306 (2013.01)

(58) Field of Classification Search
CPC ........ G01N 1/14; G01N 1/18; G01N 35/1097; G01N 35/1009; G01N 2035/00277; G01N 2035/00306; G01N 2001/1427; G01N 2001/002
USPC ...................................................... 73/863.71
See application file for complete search history.

(56) References Cited

U.S. PATENT DOCUMENTS

| | | | | |
|---|---|---|---|---|
| 4,489,779 A * | 12/1984 | Dickinson | ............. | E21B 43/129 166/105 |
| 4,600,148 A * | 7/1986 | Raymer | .................... | E03C 1/16 239/29.3 |
| 4,683,761 A * | 8/1987 | Stock | ........................ | G01N 1/14 73/864.34 |
| 4,803,869 A * | 2/1989 | Barcelona | .......... | G01N 33/1893 324/438 |
| 5,293,931 A * | 3/1994 | Nichols | .................... | E21B 43/00 166/106 |
| 5,939,330 A * | 8/1999 | Peterson | ................ | E21B 43/121 422/62 |
| 6,044,854 A * | 4/2000 | Marks | ..................... | B08B 3/006 134/111 |
| 6,232,598 B1 * | 5/2001 | Dehnert | ............. | E21B 47/1015 250/255 |
| 6,286,375 B1 * | 9/2001 | Ward | ..................... | G01N 30/12 73/19.09 |
| 6,338,282 B1 * | 1/2002 | Gilbert | ..................... | G01N 1/14 73/864.34 |
| 6,508,368 B1 * | 1/2003 | Arce, Jr. | ................. | A47J 47/20 108/24 |

(Continued)

*Primary Examiner* — Nathaniel T Woodward
(74) *Attorney, Agent, or Firm* — Jeffrey Joyce, Esq.

(57) ABSTRACT

A method of fluid sampling and device thereof, the device and method enabling the user to safely and efficiently collect fluid samples, including groundwater samples from a monitoring well, by providing a fluid sampling device that includes a container having a sampling surface and tube housing that securely holds tubing, sample containers, and other equipment and provides a drainage area so that the user may focus on collecting unadulterated samples while any fluid discharges and incidental spillage are safely captured in the container.

10 Claims, 11 Drawing Sheets

(56) References Cited

U.S. PATENT DOCUMENTS

| | | | | |
|---|---|---|---|---|
| 7,836,854 B1 * | 11/2010 | Hawkins | ............. | A01K 13/001 |
| | | | | 119/600 |
| 2006/0180302 A1 * | 8/2006 | Intelisano | ................ | E02D 1/06 |
| | | | | 166/105 |
| 2011/0005602 A1 * | 1/2011 | Harrington | ............... | E03B 1/04 |
| | | | | 137/1 |

* cited by examiner

METHOD OF FLUID SAMPLING AND DEVICE THEREOF

BACKGROUND INFORMATION

Field of the Invention

The invention relates to methods and devices for fluid sampling, including groundwater samples collected from monitoring wells.

Discussion of Prior Art

A wide array of fluids are sampled and analyzed across numerous industries. For example, water is commonly sampled and analyzed from wetland resource areas such as lakes, ponds, and streams to assess the health of an ecosystem. Residential wells and municipal water supplies are sampled and analyzed to ensure drinking water is safe to consume. Other types of fluid such as engine oil and coolant in the automotive industry are sampled and analyzed to detect the wear on certain vehicle parts. In short, fluid sampling and analysis are performed in a wide variety of settings.

One of the larger more common forms of fluid sampling is conducted in the environmental industry which involves monitoring wells used to obtain representative groundwater samples and hydrogeologic information. Groundwater sampling, and in particular low stress or low flow purging and sampling of groundwater from monitoring wells, is a common and well-known procedure that is routinely undertaken at the direction of certain environmental regulatory agencies, such as the United States Environmental Protection Agency ("EPA"), to determine the organic and inorganic loads that are transported through the subsurface under ambient flow conditions.

This groundwater sampling procedure involves extraction of groundwater from a monitoring well through the use of a pump, typically either an adjustable rate peristaltic or submersible pump; with pump selection often dictated by sample collection depth. The procedure also involves a number of separate components including a pump, tubing, a "T" connector having a valve, a flow-through-cell, a calibrated discharge container, and sample containers.

As part of this procedure, groundwater is initially pumped through tubing directly into a calibrated container to observe physical characteristics such as turbidity, coloration, and any presence of contamination, e.g.—sheen, odor, etc. The total volume of groundwater purged is recorded and the pump is turned off. The "T" connector valve is then attached to the open end of the tubing. A section of tubing is connected to one of the other open ends of the "T" connector valve which is then connected to the lower of two connection ports on a flow-through-cell. An additional section of tubing is connected to the upper connection port on the flow-through-cell which terminates into the discharge container. Sondes inserted into the flow-through-cell monitor for various indicator field parameters, e.g.—dissolved oxygen, specific conductance, temperature, pH, oxidation/reduction potential, etc., and provide calculated measurements to a meter. The remaining opening of the "T" connector valve serves as a sampling port for turbidity analysis. Water flow direction is controlled with the "T" connector valve.

In general, after determining the appropriate flow rate, groundwater is continually pumped until both depth to groundwater level and indicator field parameters are adequately stabilized. Once stabilization is achieved, groundwater samples may be collected in appropriate sample containers. Under specific regulatory guidelines, such as those promulgated by the EPA, groundwater samples are required to be collected from the tubing which is directly attached to the pump and not from the "T" connector valve or the flow-through-cell, unless otherwise authorized.

The common field collection method for obtaining such samples is surprisingly haphazard, inefficient, susceptible to inadvertent sample contamination/cross contamination, and poses a significant risk of contamination release to the surrounding environment. In the common setup, depending on the type of pump used, groundwater is pushed or pulled from a monitoring well through conventional tubing, through a "T" connector valve, through a flow-through-cell, and ultimately into a container; typically, a five-gallon bucket. All components are separated and haphazardly setup in and around the collection set. In order to shift from purging to sample collection operations, the tubing is disconnected from the "T" connector valve, after which the sampler fills sample containers from the open tubing while trying to avoid contaminating the sample and attempting to direct overflow into a bucket. The sampler must also be cognizant of the fluid within the tubing leading to and from the flow-through-cell, as well as, the flow-through-cell itself. These contents must ultimately be drained into the bucket without spilling onto the surrounding environment. This method is further complicated by the fact that the sampler in most cases is holding the tubing in one hand and the sample container in the other over a bucket, the bucket being placed beneath in hopes of catching any incidental spillage. In the specific instance when a vial is being filled and a meniscus is required, the sampler is often forced to release the tubing to free both hands to hold the sample container, maintain the meniscus, and secure the cap onto the vial. It is important to note that groundwater should continue to be pumped during the entire collection process to ensure consistency and accuracy. Filling numerous sample containers of various shapes and sizes at a reduced flow rate is often time consuming. This is exasperated by the sampler having to physically hold the tubing and/or the sample container over the discharge container during the entire collection process.

Another complication associated with this common field method is the fact that the conventional pump often generates a lot of vibration, to the point where the tubing and nearby equipment also vibrates. This creates significant instability of the overall setup, especially with regards to the tubing attached directly to the pump. Vibration is often the culprit when this tubing breaks free of the discharge container and falls to the ground, typically during either the initial purging stage or during the sample collection stage. These issues may range from an inconvenience when there is little to no contamination present, to a significant hazard when harmful biological or chemical constituents are present.

In all, this common field practice poses unnecessary risks to sample collection integrity, consistency, and efficiency. It also has the potential to cause a hazardous situation resulting from contaminants being released to the environment.

What is needed, therefore, is a sampling apparatus and method of groundwater sampling that consistently delivers unadulterated, representative samples in an efficient and secure manner.

BRIEF SUMMARY OF THE INVENTION

The invention is a fluid sampling device for use in performing a method of groundwater sampling that provides a user with a well-organized and easy to use workspace that minimizes worksite and sample contamination while optimizing the efficiency of the sampling process.

The fluid sampling device consolidates many of the separated components typical of the conventional setup and is designed to accommodate various utilities such as tubing, sampling equipment, sample containers, hardware, and other tools. A sampling surface provides a flat, sturdy surface for performing numerous sampling activities, equipped with a drainage area intended to capture all discharges including incidental spillage, which ultimately drains to a container located immediately beneath. A tube housing is provided to secure the sampling tube. The ability to secure tubing within the tube housing is critical in maintaining sample integrity and addresses the current practice of the user physically holding the tubing during sample collection. This frees the user to perform other important tasks such as filling sample containers, placing caps on containers, making tubing connections, operating meters, taking notes, preparing labels, etc. It also permits the user to temporarily leave the sampling device to oversee more than one sampling operation, when and where appropriate. Securing the tubing in the tube housing also reduces movement due to pump vibration which lessens the risk of contaminating the sample as well as the surrounding environment.

More specifically, the fluid sampling device is a container having a work surface and tube housing for use with conventional pumping systems. The sampling surface has ample room for, for example, holding a flow-through-cell and containers that are need for sampling. The tube housing is provided for securing and positioning the tubing that comes from a conventional well pump and delivers the fluid to the device, the tube housing positioned above the work surface. The drainage area is a part of the work surface and causes discharges and incidental spillage to pass through the work surface and into the body of the container.

Once the fluid sampling device is in position at a sampling site and a pump having tubing is connected to a well, the end of the tubing opposite the pump is secured in the tube housing, above the sampling surface, and the pump activated thereby delivering fluid to the container. In general, a conventional "T" connector valve is used to easily allow a user to direct fluid from the well through a flow-through-cell or into a turbidity sample container. The user does not need to continuously hold equipment during the collection process and is therefore free to focus attention elsewhere to efficiently complete the sampling while reducing the risk of sample contamination and site contamination.

BRIEF DESCRIPTION OF THE DRAWINGS

The present invention is described with reference to the accompanying drawings. In the drawings, like reference numbers indicate identical or functionally similar elements. The drawings are not drawn to scale.

DETAILED DESCRIPTION OF THE INVENTION

The present invention will now be described more fully in detail with reference to the accompanying drawings, in which the select embodiments of the present disclosure are shown. This disclosure should not, however, be construed as limited to the particular embodiments set forth herein or illustrated in the accompanying drawings; rather, the embodiments described herein are provided so that this disclosure will be complete and will fully convey the scope of the invention to those skilled in the art.

FIGS. 1-11 illustrate a fluid sampling device 100 for use in performing a method 1000 of groundwater sampling. The device 100 includes a base container 10, a sampling surface 20 and a tube housing 50. The method 1000 incorporates a conventional pump P and tubing T to deliver fluid from a well (not shown) into the fluid sampling device 100, whereby the conventional tubing T that exits the pump P is secured in the tube housing 50 above the base container 10 for fluid sample collection. This disclosure largely discusses the fluid sampling device 100 in terms of its use in collecting groundwater samples from a monitoring well, however, it is understood that the fluid sampling device 100 may be used with any number of different kinds of fluids and is not in any way limited to groundwater.

Figure 4:
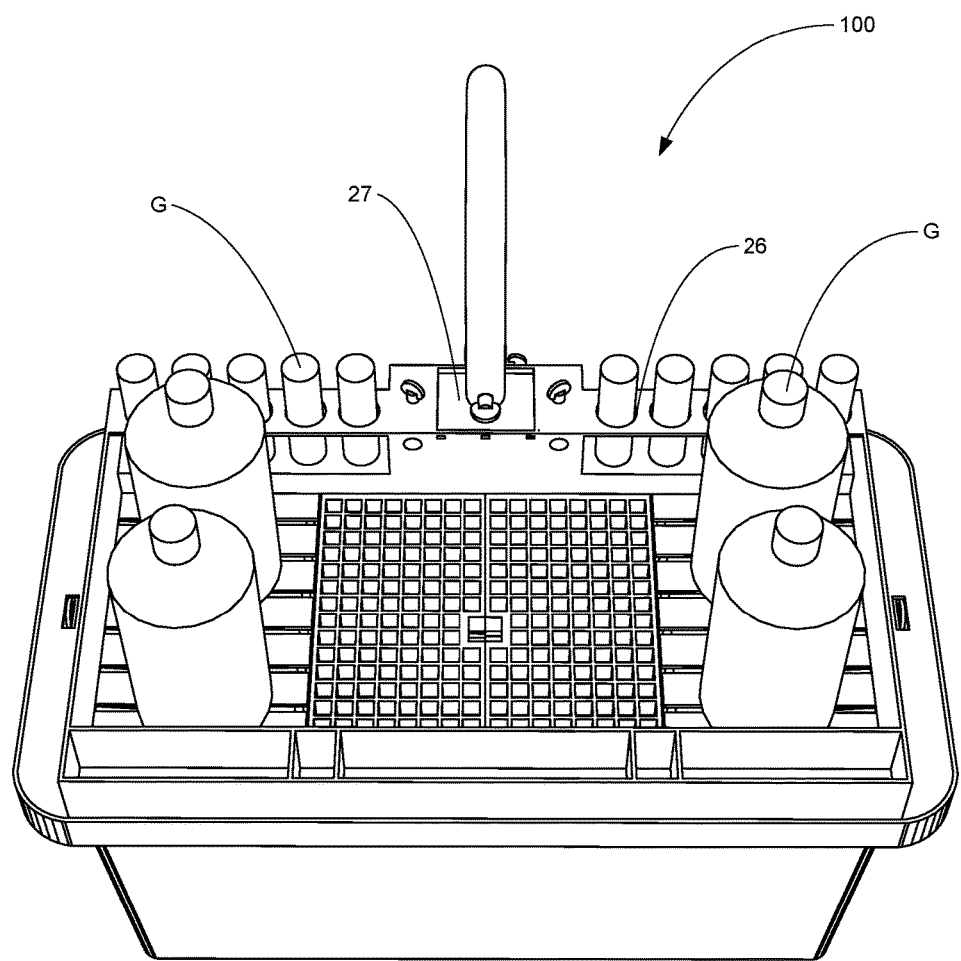
FIG. 4 is a front perspective view of the first embodiment showing a number of sample containers positioned on and in the device.
Figure 5:
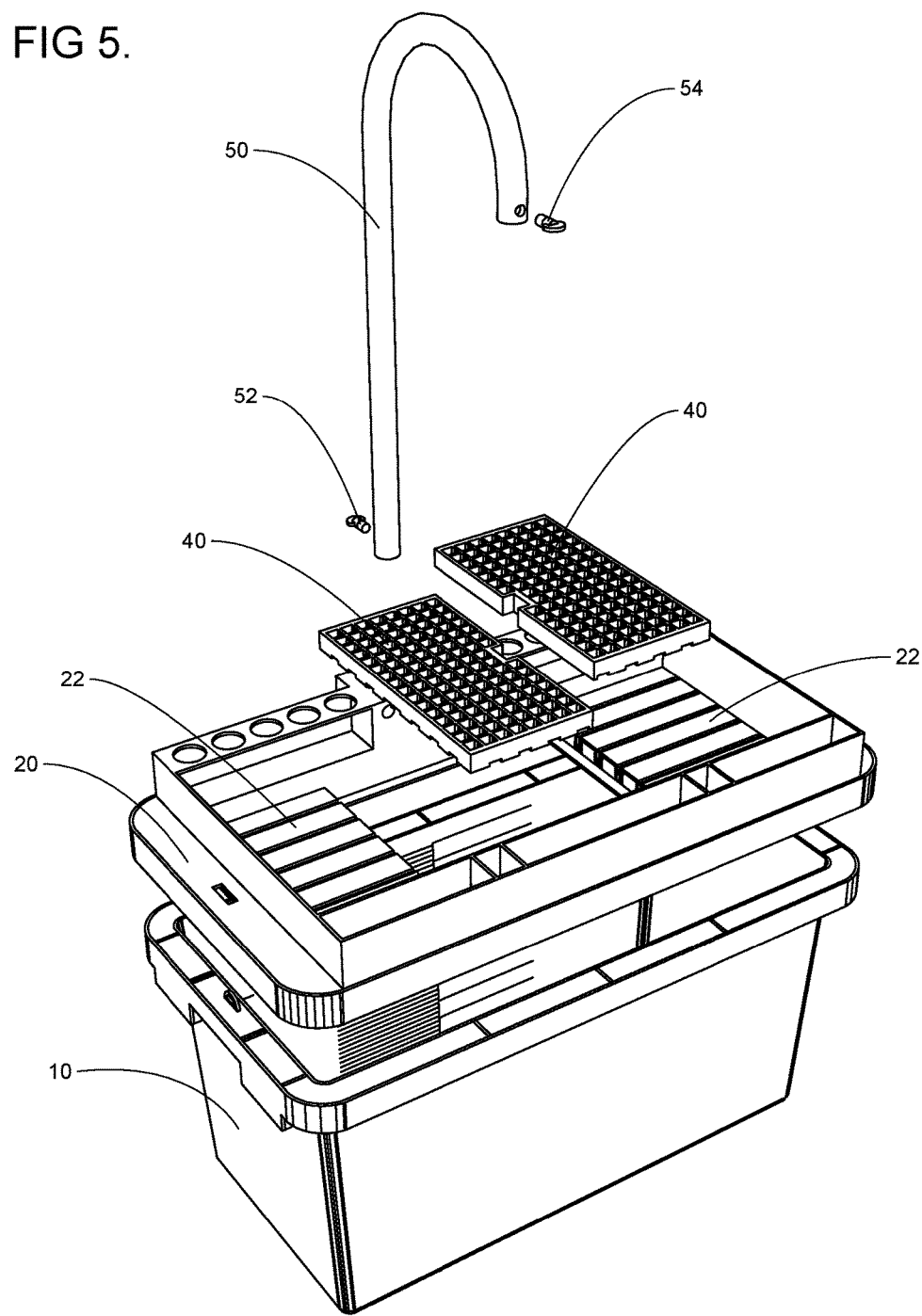
FIG. 5 is an exploded view of the first embodiment showing the separable components separated.
Figure 8:
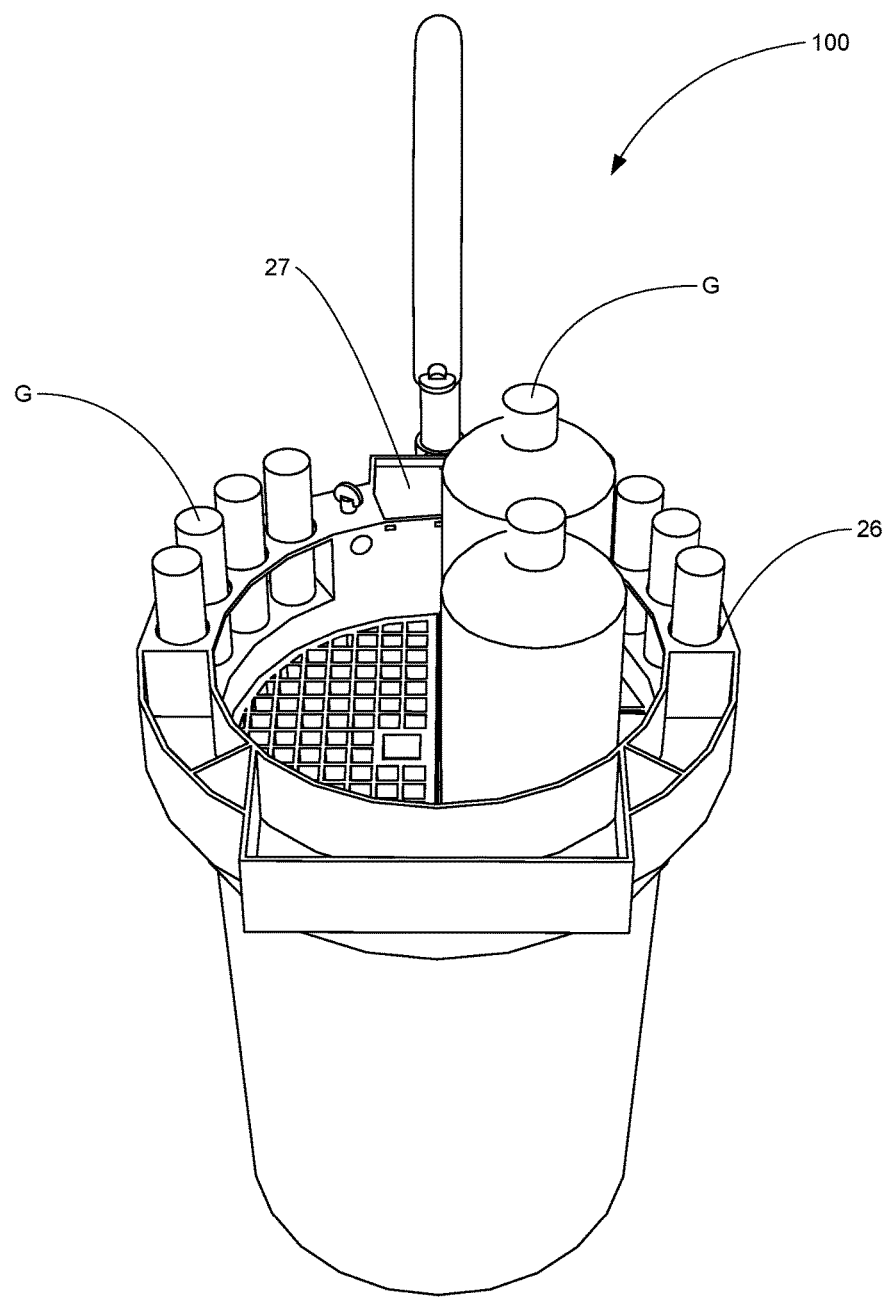
FIG. 8 is a front perspective view of the second embodiment holding a number of sample containers.
Figure 9:
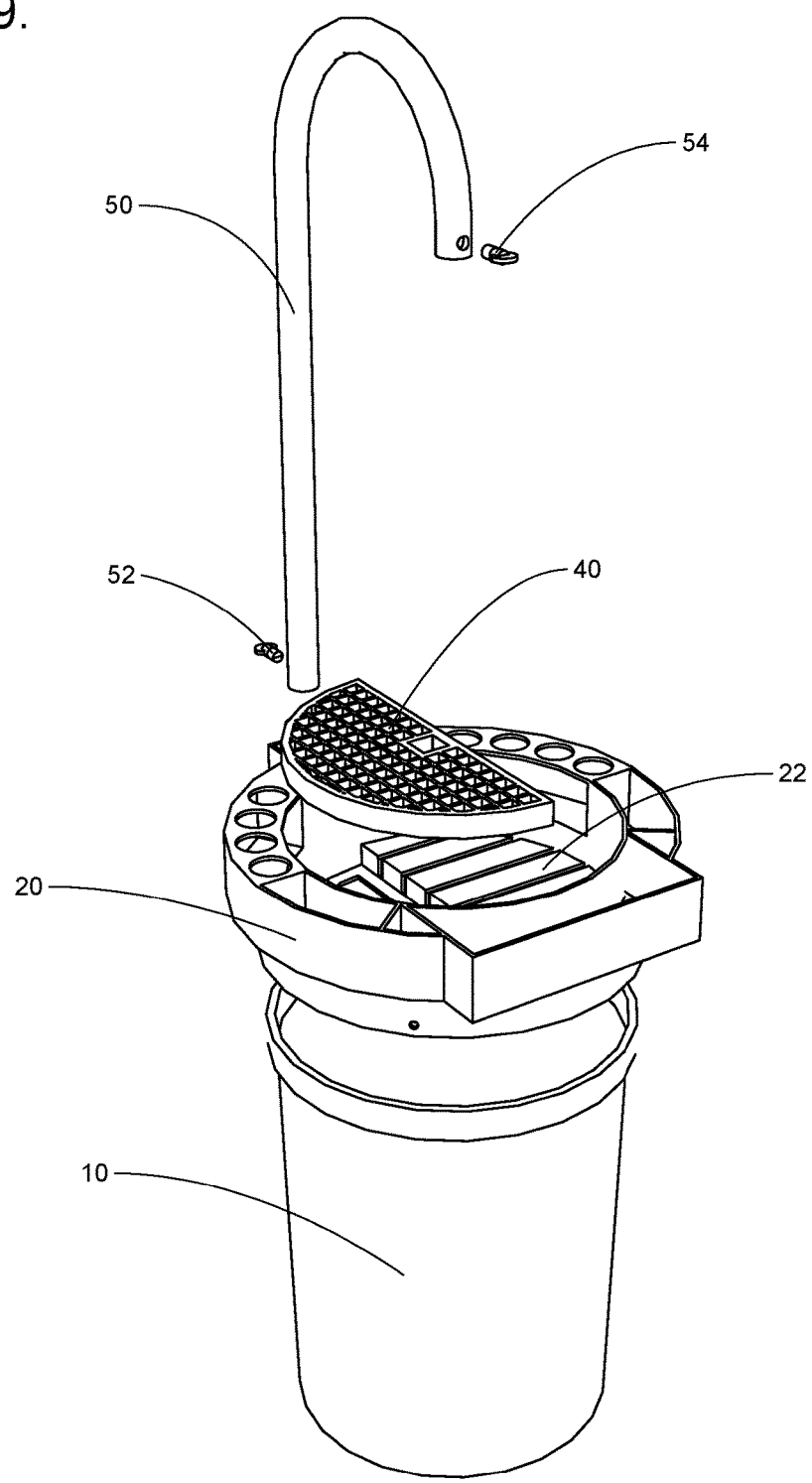
FIG. 9 is an exploded view of the second embodiment showing the separable components separated.

The fluid sampling device 100 and method 1000 allow a user to collect groundwater samples in a number of sample containers G, shown in FIGS. 4 and 8, without having to handle the tubing T that is delivering the fluid, and any fluid that does not go into the sample containers G is captured by the container 10. Allowing the user to focus on filling sample containers G reduces the risk of sample contamination and having the tubing T discharge the fluid above the container 10 eliminates the risk of contaminating the surrounding environment. Additional tubing T is also provided beneath the tube housing 50 to convey fluid through a flow-through-cell C and back into the container 10. This, again, increases efficiency and reduces the risk of spillage to the environment.

The container 10 is a water tight container and may be any suitable shape and size. For example, a conventional five-gallon bucket, illustrated in FIGS. 6-9, that is made of a conventional water-proof plastic may be suitable, as are rectangular plastic totes, illustrated in FIGS. 1-5. During the sampling all discharges and/or incidental spillage falls into the container 10.

The sampling surface 20 is securable on top of the container 10, for example, in the embodiment shown it is secured in place in the same manner as conventional bucket or tote covers, however additional fasteners may also be used instead of or in addition to this conventional approach. The sampling surface includes a work area 22 and a number of holders 26, 27, 28. The sampling surface is also equipped with a drainage area 40 which may be constructed in any suitable manner that allows fluids to drain through the surface while allowing the surface to have the structural strength necessary to hold conventional fluid containers. For example, the drainage area shown in the figures is a grate-like or lattice-like structure whereby a number of strips of material are crossed and/or fastened together, thereby providing a surface area that containers or tools may be placed upon but also having a number of openings to allow fluid to pass into the inside of the container 10. A relatively large opening 42 is provided so that a drainage tube T3 may be directly placed inside the container 10. The drainage area 40 may be made of a number of suitable conventional materials, such as, for example, plastic. The drainage area 40 may be removable as to allow easy access to the inside of the container 10. In the embodiment shown in FIGS. 1-5 the drainage area 40 is comprised of two separate and removable components, whereas the drainage area in the embodiment shown in FIGS. 6-9 is a single removable component.

The holders 28 are designed to securely hold tools and equipment commonly used during sampling activities such as writing utensils, logbooks, tape measures, calculators, stopwatches, etc. In general, the holders 28 are sized and shaped to hold those commonly used tools, while other individual holders 26 are shaped to hold conventional sample containers G that are commonly used in the method 1000. A flat surface 27 is also included to provide a temporary holding location for sample container caps so that the user has a relatively sterile and secure location to store caps after removal from their respective containers during sample collection activities.

Figure 10:
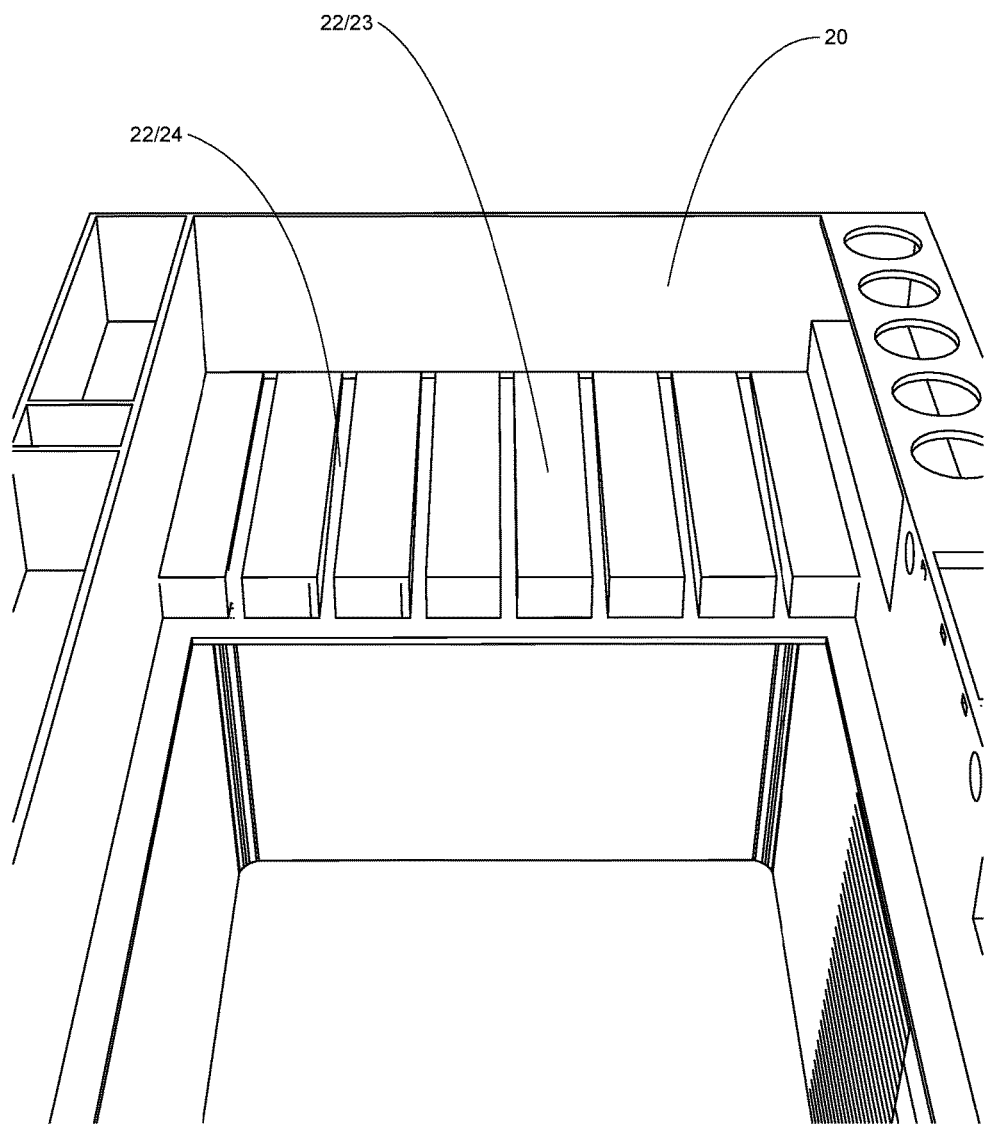
FIG. 10 is a partial front view of the work surface for the embodiment.

The work area 22 may be comprised of one or more level members 23 that are separated by one or more slots 24 that are slanted towards the drainage area 40, as shown in FIG. 10, such that any discharge or incidental spillage is directed into the drainage area 40. The work area 22 may also be a solid platform.

Figure 3:
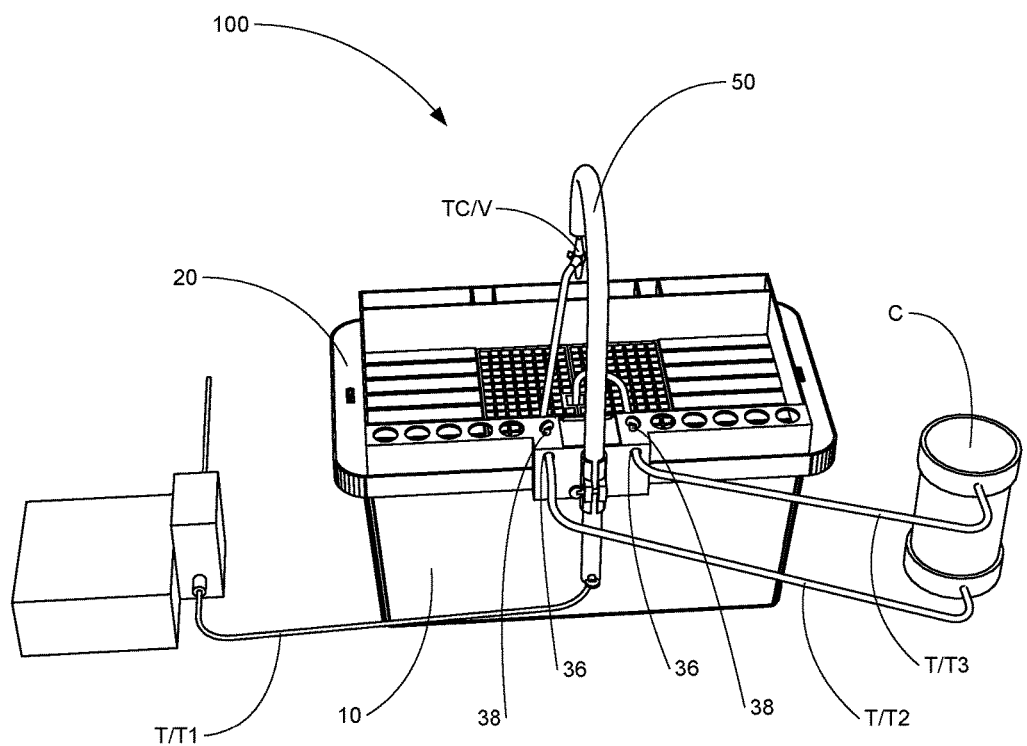
FIG. 3 is a top and rear perspective view of the first embodiment where the flow-through-cell is positioned outside of the device.
Figure 6:
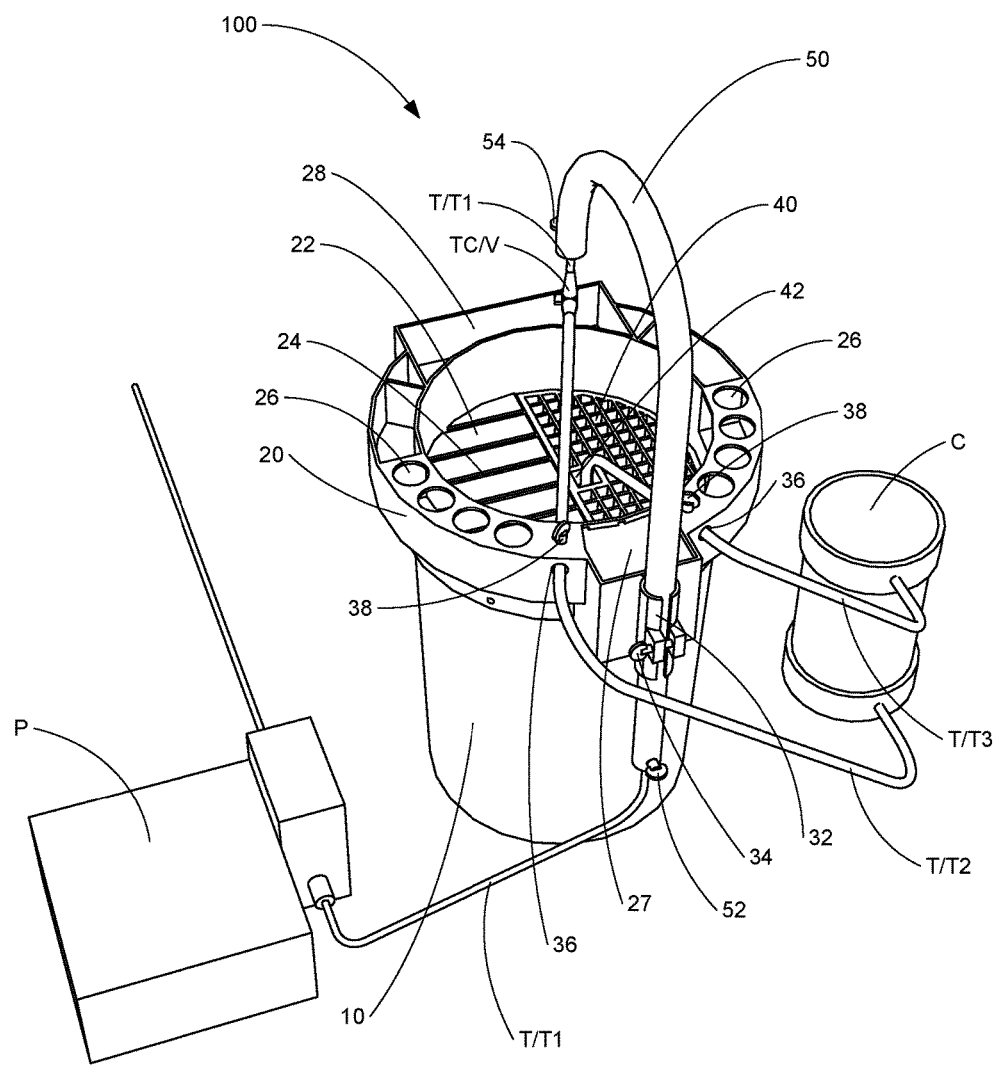
FIG. 6 is a rear perspective view of the second embodiment of the device with a flow-through-cell located outside of the device.
Figure 7:
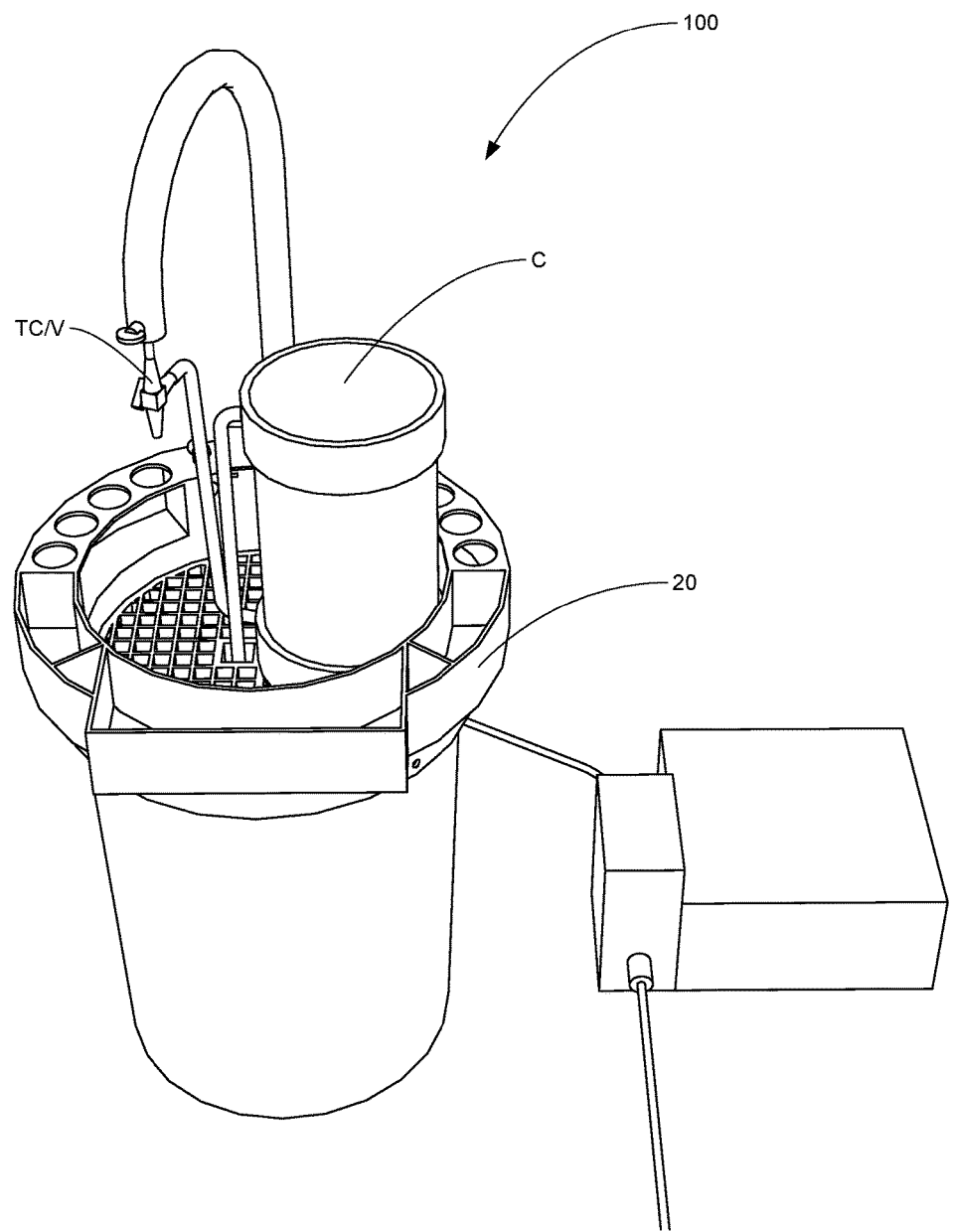
FIG. 7 is a front perspective view of the second embodiment of the device where the flow-through-cell is located on the work surface.

Additional openings 36 may be provided in the sampling surface 20 to secure tubing T. For example, FIGS. 3 and 6 illustrate a setup where a flow-through-cell C is positioned outside of the device, and delivery tubing T2 and return tubing T3 are secured in openings 36 by securing means 38. The securing means 38 may be any suitable securing means such as conventional clamping devices or they may be threaded fasters that are inserted to a depth that lightly presses on the tubing to hold it in position.

Figure 1:
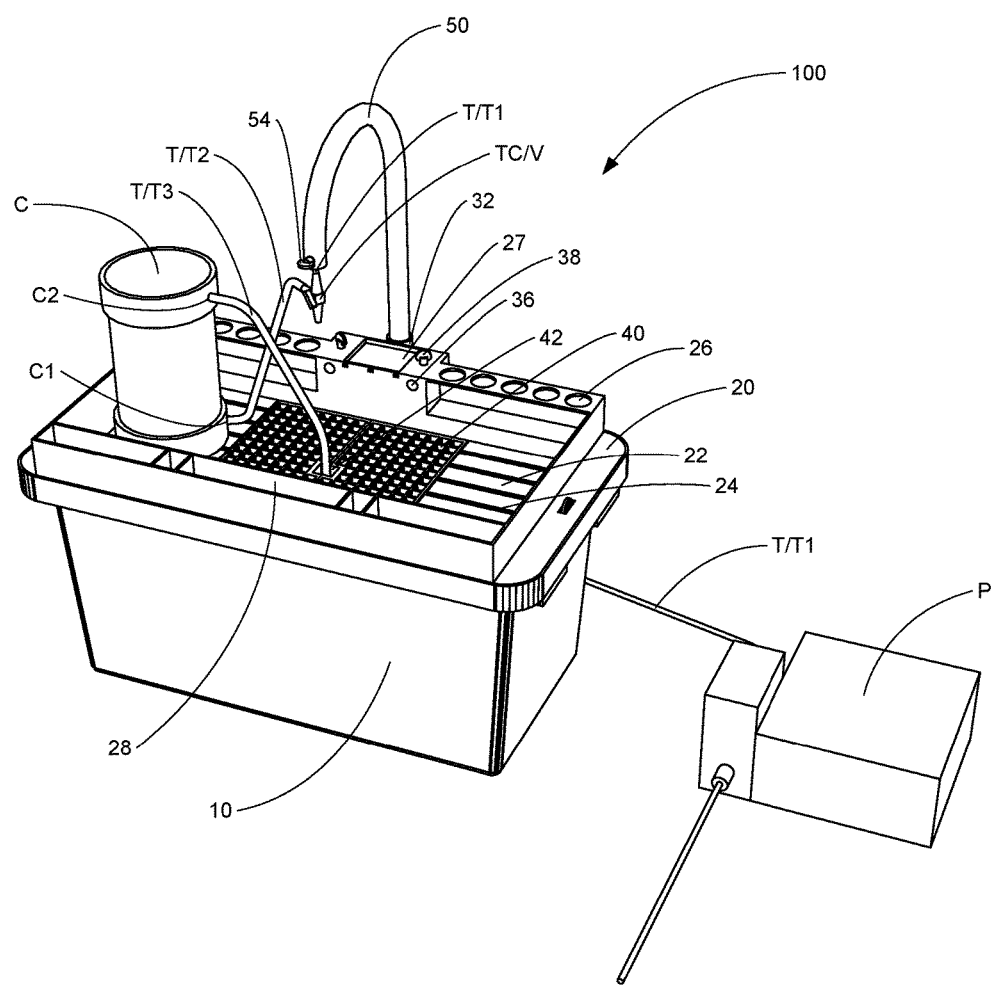
FIG. 1 is a front perspective view of a first embodiment of the device according to the invention connected to a conventional pump and having a flow-through-cell located within the device.
Figure 2:
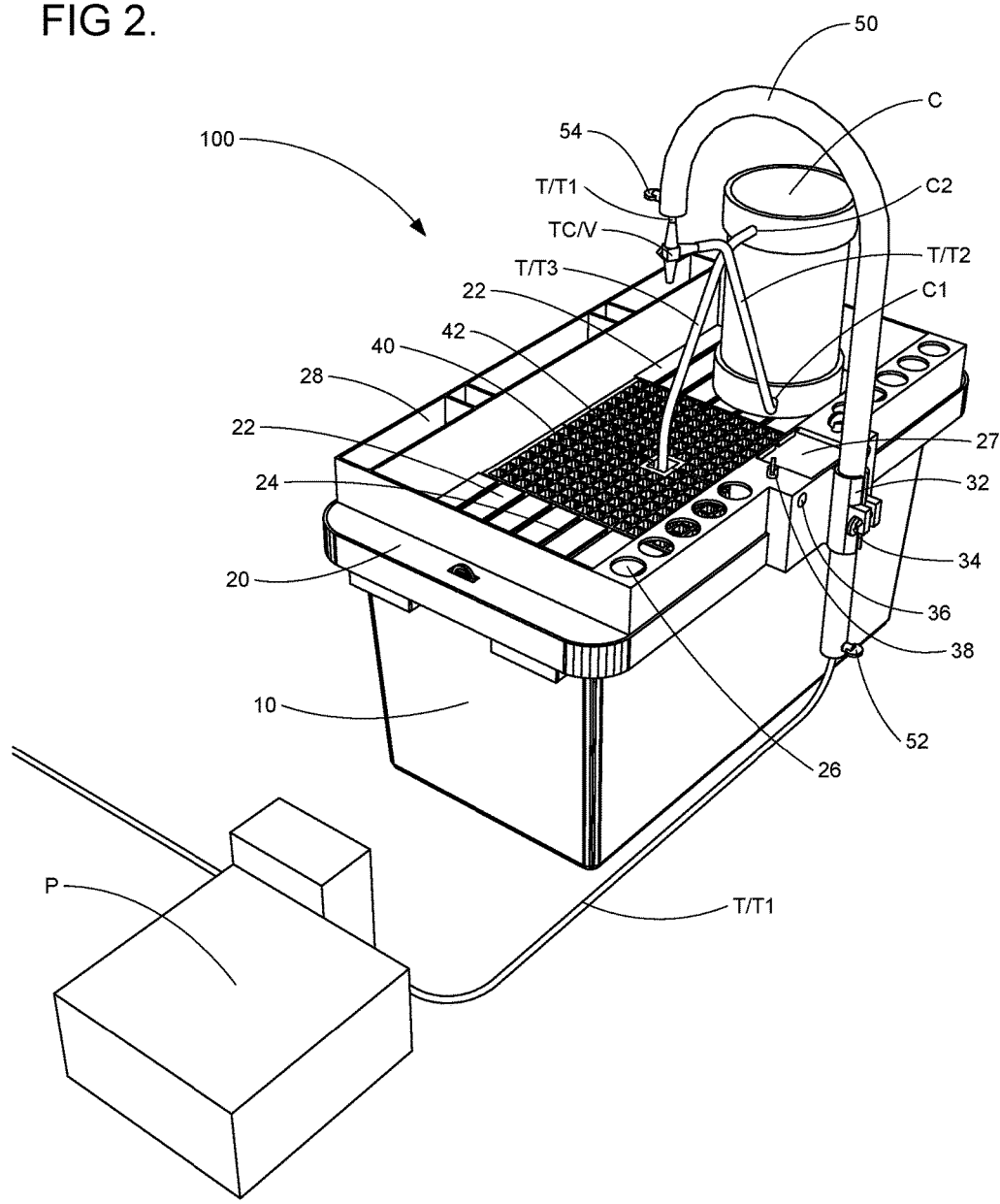
FIG. 2 is a rear and side perspective view of the first embodiment of the device.
Figure 11:
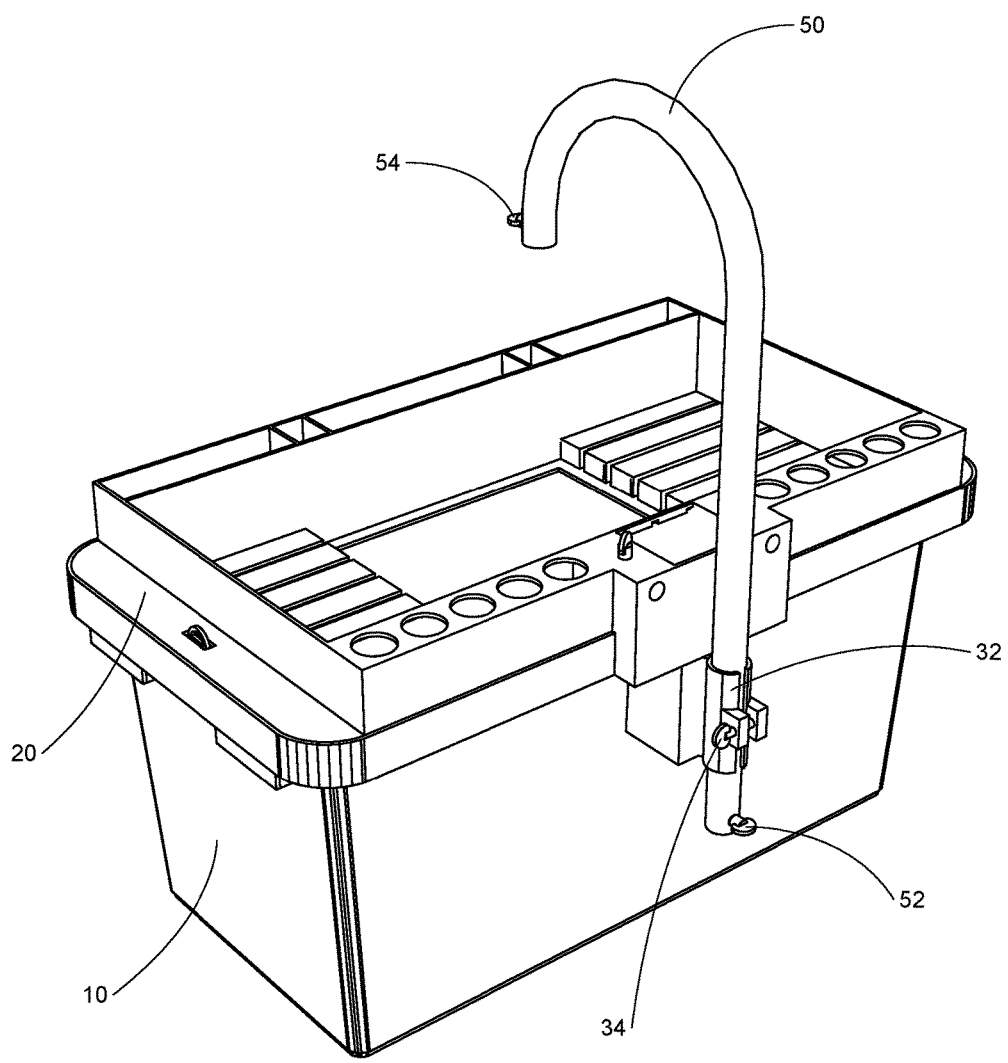
FIG. 11 is a rear perspective view of the device showing the tube housing mounted on the container.

In the embodiment shown, the tube housing 50 is a ridged conduit that is adjustably connected to the sampling surface 20 and is slightly larger in size then the tubing T used with the conventional pump P which is secured in position with a conventional clamping device 32. The tube housing 50 may also be affixed to the container 10 rather than the sampling surface 20 as is shown in FIG. 11. While adjustability is beneficial the tube housing may also be affixed in a fixed position using conventional means. The tubing T1 that extends out of the pump P is inserted through the tube housing 50 and secured at the inlet 52 and outlet 54 such that the tube housing 50 acts like a faucet to discharge fluid above the container 10. FIGS. 1 and 6 illustrate the use of a "T" shaped connector valve TC. The "T" shaped connector having a valve, conventionally referred to as a "T" connector valve, is an open water-proof connector with three openings, i.e. one for fluid input and two fluid outputs with a valve V in place so as to allow the user to direct the incoming fluid to either or both of the two outputs.

As shown in FIGS. 1-3, 6 and 7, the "T" connector valve TC allows the user to direct the flow of fluid either through the tubing T2 and into the flow-through-cell C, or directly out of the "T" connector valve TC where it is discharged above the drainage area 40. The tube housing 50 is also adjustable and may be moved in either the vertical or horizontal planes, i.e. up or down and side to side, by loosening and then securing of the clamping device 32, best shown in FIGS. 2 and 6, thereby accommodating a wide array of sampling positions. Securing means 52, 54 secure the tubing T1 in the tube housing 50. The securing means 52, 54, may be any suitable securing means such as, for example, threaded fasteners that press the tubing T1 against the inside of the tube housing 50.

The method 1000 of collecting groundwater samples uses the device 100 to collect samples of groundwater from a monitoring well using a pump P. The pump P is a conventional pump that is able to deliver groundwater from the monitoring well and has tubing T1 that is connectable to the tube housing 50 in the groundwater sample collection device 100. Specifically, tubing T1 is inserted into and through the tube housing 50 and secured in place using securing means 52, 54 so that the end of tubing T1 is above the surface 20. One end of a "T" connector valve TC is inserted into and connected to tubing T1, and one end of a flow-through-cell delivery tubing T2 is connected to another end of the "T" connector valve TC. A second end of the flow-through-cell delivery tubing T2 is connected to a flow-through-cell C by input port C1. Tubing T3 returning from the flow-through-cell C connects a flow-through-cell outlet port C2 to the container 10. Activating the pump delivers groundwater through tubing T1 to the "T" connector valve in the housing 50 above the sampling surface 20, where the user may decide to direct the water through the flow-through-cell C for monitoring, ultimately returning the water back to the container 10 or the user may send the water directly through the "T" connector valve and fill any number of containers to conduct turbidity analysis. Ultimately, samples may be collected from the open end of tubing T1 after disconnecting the "T" connector valve TC from tubing T1.

It is understood that the embodiments described herein are merely illustrative of the present invention. Variations in the construction or implementation of the method of groundwater sampling and device thereof may be contemplated by one skilled in the art without limiting the intended scope of the invention herein disclosed and as defined by the following claims.

What is claimed is:

1. A device adapted to assist a user in collecting and testing fluid samples from fluid, the fluid being delivered to the device from a pump having pump tubing that delivers the fluid from a fluid source, the device comprising:
    a discharge container, a sampling surface situated on top of the discharge container, and a fluid tube housing, the fluid tube housing having an inlet and an outlet, the outlet positioned above the sampling surface, the pump tubing inserted in the fluid tube housing through the inlet and out through the outlet and secured above the sampling surface in the fluid tube housing such that a space exists between the sampling surface and the outlet that is an unenclosed sampling area;
    wherein the sampling surface includes a work area and a drainage area, the work area sized to hold one or more sample containers and/or testing equipment and the drainage area having one or more openings; and wherein as the pump delivers the fluid from the fluid source through the pump tubing the fluid exits the pump tubing for collection and testing by the user above the sampling surface and wherein the fluid that exits the pump tubing and is not collected or tested by the user passes through the one or more openings in the drainage area and into the discharge container beneath the sampling surface.

2. The device of claim 1, wherein the fluid tube housing is a ridged conduit that is adjustable in the horizontal and vertical planes.

3. The device of claim 2, wherein the fluid tube housing is mounted to the sampling surface.

4. The device of claim 2, wherein the fluid tube housing is mounted to the discharge container.

5. The device of claim 2, wherein the sampling surface includes one or more holders that are sized to securely hold tools, equipment and sample containers.

6. The device of claim 5, wherein the work area includes one or more level members that are separated by one or more slots that are slanted towards the drainage area and wherein fluid contacting the work area is directed into the drainage area where it falls into the discharge container.

7. The device of claim 6, wherein a first end of a "T" connector valve is connected to the pump tubing exiting the outlet of the fluid tube housing, a second end of the "T" connector valve is positioned above the sampling surface, and a third end of the "T" connector valve is connected to a flow-through cell via an additional section of tubing.

8. The device of claim 7, wherein one or more openings are provided in the sampling surface that secures tubing that is connected to external components.

9. A method of groundwater sampling comprising:
a) pumping groundwater from a well through a sample delivery tube, the sample delivery tube having a first end connected to the well and a second end through which the groundwater is pumped;
b) providing a device adapted to assist a user in groundwater sampling and testing that includes a discharge container, a sampling surface situated on top of the discharge container that includes a work area and a drainage area, and a fluid tube housing that secures the sample delivery tube and positions the second end of the sample delivery tube above the sampling surface;
c) activating the pump;
d) collecting groundwater samples in one or more sample containers from the second end of the sample delivery tube above the sampling surface.

10. The method of claim 9, wherein step d includes the following steps:
d1) attaching a first end of a "T" connector valve to the second end of the sample delivery tube;
d2) connecting a second end of the "T" connector valve to a first end of a flow tube, the flow tube having a second end that is connected to an input opening on a flow-through-cell and connecting an output opening on the flow-through-cell to a first end of outflow tubing, the outflow tubing having a second end that is inserted into the discharge container;
d3) using the third end of the "T" connector valve to fill one or more sample containers;
d4) disconnecting the "T" connector valve and collecting groundwater samples directly from the second end of the sample delivery tube.

\* \* \* \* \*